United States Patent [19]

Matsuo et al.

[11]  4,343,953
[45]  Aug. 10, 1982

[54] METHOD FOR PREPARING 4-HYDROXY-3-METHYL-2-(2-PROPYNYL)-2-CYCLOPENTENOLONE

[75] Inventors: Noritada Matsuo, Itami; Nobushige Itaya, Nishinomiya; Kohichi Aketa, Kawanishi; Osamu Magara, Osaka; Toshio Nishioka, Ashiya, all of Japan

[73] Assignee: Sumitomo Chemical Company, Limited, Osaka, Japan

[21] Appl. No.: 159,497

[22] Filed: Jun. 16, 1980

[30] Foreign Application Priority Data

Jun. 22, 1979 [JP] Japan ............................ 54-79311
Jul. 16, 1979 [JP] Japan ............................ 54-90778
Aug. 6, 1979 [JP] Japan ............................ 54-100550

[51] Int. Cl.$^3$ .................................................. C07C 45/45
[52] U.S. Cl. .................................. 568/347; 560/176; 568/396; 568/390; 568/413
[58] Field of Search .............. 560/176; 568/396, 390, 568/347, 397

[56] References Cited

U.S. PATENT DOCUMENTS

| | | | |
|---|---|---|---|
| 3,591,643 | 7/1971 | Fanta et al. | 568/347 |
| 3,701,814 | 10/1972 | Shilling | 560/176 |
| 3,824,272 | 7/1974 | Brossi et al. | 568/390 |
| 3,914,289 | 10/1975 | Akutogawa et al. | 568/397 |
| 3,972,943 | 8/1976 | Kunstlo et al. | 568/396 |
| 4,173,707 | 11/1979 | Torii et al. | 560/176 |
| 4,245,122 | 1/1981 | Yoshida et al. | 568/397 |

OTHER PUBLICATIONS

Kurono et al., Chem. Abst., vol. 90, #86704a (1979).
Ite et al., Chem. Abst., vol. 91, #56450t (1979).
Muramoto et al., Chem. Abst., vol. 79, #41727s (1973).
Muramoto et al., Chem. Abst., vol. 82, #139218p (1975).
Calame et al., Chem. Abst., vol. 80, #3172v (1974).

Primary Examiner—Natalie Trousof
Assistant Examiner—James H. Reamer
Attorney, Agent, or Firm—Stevens, Davis, Miller & Mosher

[57] ABSTRACT

The present invention relates to a novel method for producing cyclopentenolone of the formula (I),

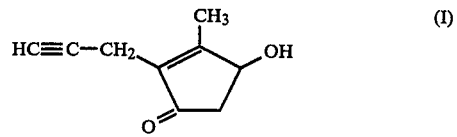

which is a useful intermediate for producing agricultural chemicals, which comprises reacting an acetonedicarboxylic ester of the formula (VII),

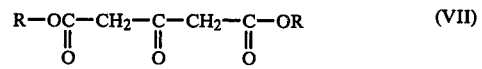

wherein R is a $C_1$-$C_6$ alkyl group, with 2-propynyl chloride in the presence of magnesium alkoxide and in the presence of alkali iodide to obtain novel mono-(2-propynyl)-substituted acetonedicarboxylic ester of the formula (VI),

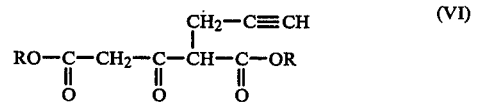

wherein R is as defined above; hydrolyzing the mono-(2-propynyl)-substituted acetonedicarboxylic ester of the formula (VI) under alkaline conditions with an alkali and then reacting the hydrolyzed product with methylglyoxal of the formula,

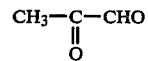

to obtain novel γ-diketone of the formula (V),

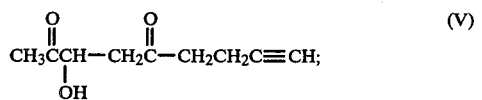

and ring-closing the γ-diketone of the formula (V) under alkaline condition.

21 Claims, No Drawings

METHOD FOR PREPARING 4-HYDROXY-3-METHYL-2-(2-PROPYNYL)-2-CYCLOPENTENOLONE

The present invention relates to a method for producing cyclopentenolone.

More particularly, it provides a novel method for producing cyclopentenolone of the formula (I),

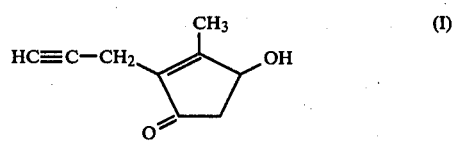

which is a useful intermediate for producing agricultural chemicals.

Allethrin of the formula (II),

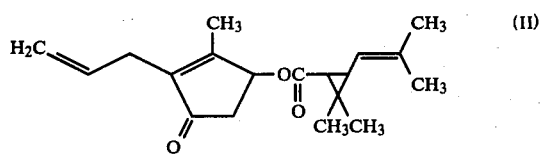

known as a useful agricultural chemical was invented by M. S. Schecher in 1949, and it has widely been used in the world because of its excellent insecticidal activity and low toxicity. Many well known methods exist for synthesizing the alcohol moiety of allethrin, i.e. allethrolone of the formula (III)

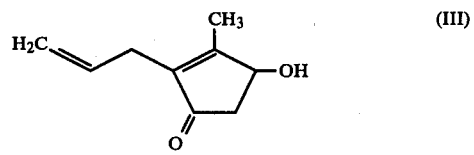

While it is well known that esters resulting from cyclopentenolone of the formula (I), having a similar structure to allethrolone, and various acids, have also a strong insecticidal activity like allethrin, and particularly that the compound of the formula (IV),

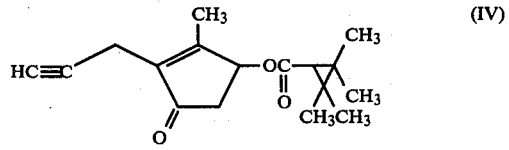

which is an ether resulting from cyclopentenolone and 2,2,3,3-tetramethylcyclopropanecarboxylic acid, has extremely strong knock-down and lethal effects (Published Examined Japanese Patent Application No 15843/1975), There is no literature on the synthesis of cyclopentenolone of the formula (I).

The inventors extensively studied a method for producing cyclopentenolone of the formula (I), and found a very advantageous method. The inventors made a further study of this method and completed the present invention.

The processes of this invention are roughly illustrated as follows:

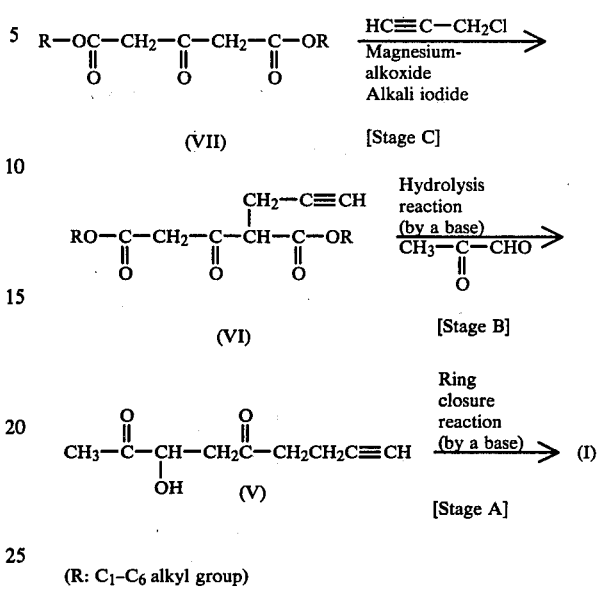

(R: $C_1$–$C_6$ alkyl group)

Next, the present invention will be illustrated in more detail as follows:

[Stage A]

The present invention provides a novel method for producing cyclopentenolone of the formula (I) characterized in that γ-diketone of the formula (V),

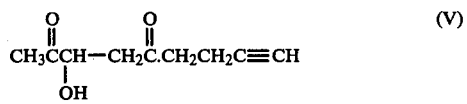

is subjected to ring-closure reaction under alkaline conditions.

In carrying out the method of the present invention, alkali hydroxides (e.g. sodium hydroxide, potassium hydroxide, lithium hydroxide) and alkali carbonates (e.g. sodium carbonate, potassium carbonate) are popularly used as reagents for making the reaction system alkaline. Soluents commonly used in the present invention, include, for example, water, methanol, ethanol, propanol, tetrahydrofuran, dioxane, dimethylformamide, dimethyl sulfoxide, benzene, toluene, xylene, hexane, chloroform and dichloromethane. Of course, mixtures of these solvents may be used. When the reaction is carried out in a heterogeneous organic solvent/water system, phase transfer catalysts such as benzyltrimethylammonium chloride, benzyltrimethylammonium bromide, trimethylstearylammonium chloride and the like may be used.

The reaction time is generally 15 minutes to 10 hours. The reaction temperature is not particularly limited, but generally, it is within a range of −30° C. to room temperature (e.g. 20° C.). A preferred amount of the alkali is 0.5 to 2.0 times by mole based on the compound of the formula (V).

[Stage B]

The present invention relates to a method for producing γ-diketone.

More particularly, it provides a novel method for producing novel γ-diketone of the formula (V),

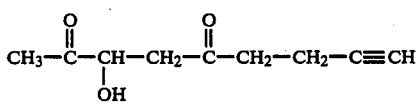

For the synthesis of cyclopentenolone (I), we may think the method shown in Scheme I which follows a synthetic method for allethrolone (refer to Scheme A) now in practical use in industry.

Scheme A:

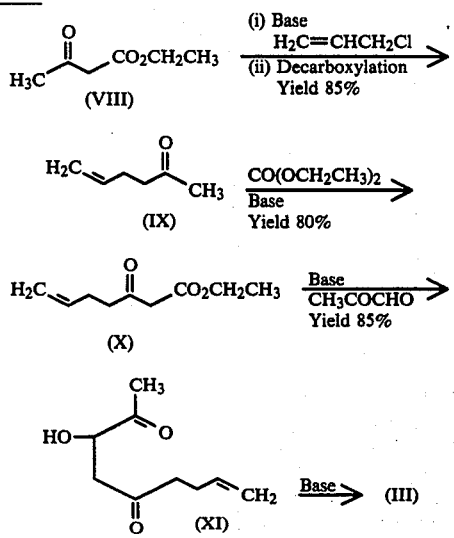

Scheme I:

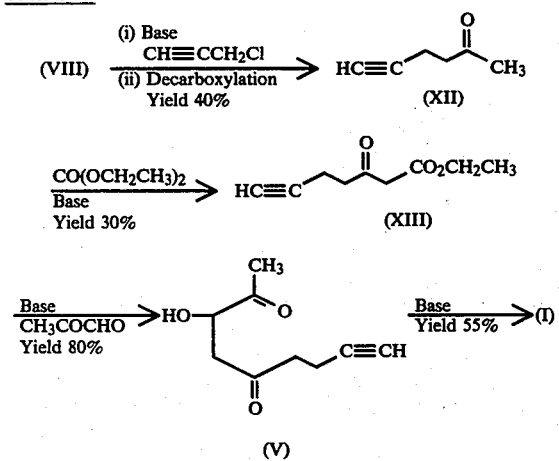

Scheme I is a modification of Scheme A in which propargyl chloride is used in place of allyl chloride. It is not however practical, because its overall yield from a starting material, ethyl acetoacetate (VIII), to a final product, cyclopentenolone (I), is as extremely low as 5%. Particularly, the yields of the intermediate compounds (XII) and (XIII) are 40% and 30%, respectively, being extremely low as compared with those of the corresponding allyl-substituted compounds (IX) and (X) in Scheme A. Consequently, the overall yield from ethyl acetoacetate (VIII) to γ-diketone (V) is only 9.6%, which is a serious weak point of this method.

Another method for synthesizing γ-diketone (V) may be one in which the dianion of ethyl acetoacetate (VIII) is used (Scheme II).

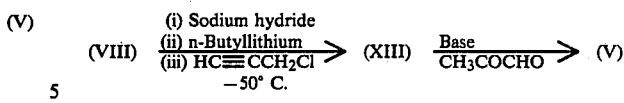

This method is one which comprises reacting ethyl acetoacetate (VIII) with sodium hydride and n-butyllithium to produce a dianion, reacting the dianion with propargyl halide to obtain a compound (XIII) and then reacting the compound (XIII) with methylglyoxal in the same manner as in Scheme I to obtain γ-diketone (V).

This method gives a high overall yield (48%) from ethyl acetoacetate (VIII) to γ-diketone (V) as compared with Scheme I, but it has the following serious drawbacks:

(1) A super-low temperature such as −50° C. is required at the alkynylation step.

(2) n-Butyllithium, which is not easy to handle in industry, must be used.

Consequently, this method is not always satisfactory from the industrial point of view.

For the reasons as described above, the inventors extensively studied a method for producing γ-diketone (V) which is an important intermediate for the synthesis of cyclopentenolone (I) used as an intermediate for insecticidal compounds, and found a very advantageous method. The inventors made a further study of this method and completed the present invention.

The present invention provides a novel method for producing γ-diketone of the foregoing formula (V) characterized in that mono-(2-propynyl)-substituted acetonedicarboxylic esters of the formula (VI),

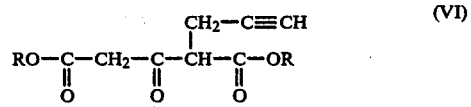

wherein R is a C₁–C₆ alkyl group, is hydrolyzed under alkaline conditions and then allowed to react with methylglyoxal of the formula,

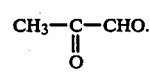

The following is a well known synthetic method for γ-diketone (XI), an intermediate for allethrolone, which is similar to the method of the present invention (U.S. Pat. No. 2,768,967):

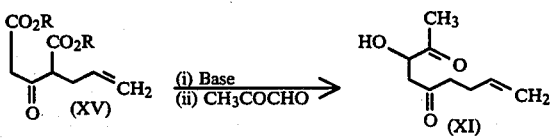

However, the yield of this method described in the literature is only 26%, and the result of the inventors' follow-up experiment also showed as extremely low a yield as 30%. This method was not therefore employed for the commercial production of allethrolone.

The inventors unexpectedly found that, when a propargyl-substituted compound (VI) is used in place of the compound (XV), γ-diketone (V) can be obtained in a high yield exceeding 80%. The inventors made a further study of this method and completed the present invention.

In the formula (VI) representing acetonedicarboxylic ester derivatives, R represents for example methyl, ethyl, n-propyl, isopropyl, n-butyl, n-pentyl and n-hexyl groups.

As reagents used for hydrolysis in the present invention, alkali hydroxides such as sodium hydroxide, barium hydroxide, lithium hydroxide, potassium hydroxide and the like are preferred. The solvent used for the reaction of the present invention includes for example water, lower alcohols such as methanol, ethanol or propanol and hydrocarbons (e.g. hexane, benzene, toluene, xylene) and mixtures thereof.

In the present invention, the reaction temperature is within a range of $-20°$ C. to the boiling point of the solvent. Generally, however, reaction temperatures between 0° C. and 50° C. are preferred, and those between 30° C. and 40° C. are most preferred.

The reaction time is within a range of preferably 5 hours to 50 hours.

The method of the present invention consists of two reaction steps, i.e. hydrolysis of the compound (VI) and reaction between the hydrolyzed product and methylglyoxal. However, carrying out the two steps continuously without the separation of the hydrolyzed product is preferred in terms of industrial practice and yield.

In the reaction between the hydrolyzed product and methylglyoxal, the yield varies with the pH of the reaction solution, and the most preferred pH is within a range of 7 to 8.

The molar ratio of the reagents used in the present invention need not be particularly limited, but the amounts of the alkali and methylglyoxal are preferably 2.0 to 4.0 times by mole and 1.0 to 2.0 times by mole, respectively, based on the acetonedicarboxylic ester derivatives of the formula (VI).

As described above, the present invention provides a method for producing $\gamma$-diketone (V), which is an important intermediate for the synthesis of cyclopentenolone (I) used as an important intermediate for agricultural chemicals, with ease and in a high yield. The role of the present invention is extremely great at the present time at which there is no advantageous method for producing cyclopentenolone (I).

[Stage C]

The present invention relates to a method for producing mono(2-propynyl)-substituted acetonedicarboxylic esters of the formula (VI),

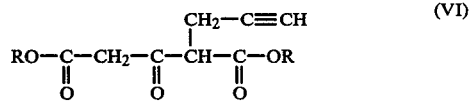

(VI)

wherein R is a $C_1$–$C_6$ alkyl group. More particularly, it relates to a method for producing mono(2-propynyl)-substituted acetonedicarboyxlic esters of the formula (VI) characterized by reacting 2-propynyl chloride with an acetonedicarboyxlic ester of the formula (VII),

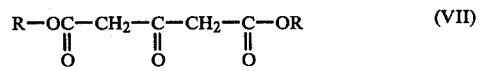

(VII)

wherein R is as defined above, in the presence of magnesium ($C_1$–$C_2$)-alkoxide and in the presence of alkali iodide.

As to the conventional methods for obtaining monosubstituted acetonedicarboxylic esters, a synthetic method for the monoalkyl-, monoallyl- and monoaralkyl-substituted compounds is disclosed, for example, in Nogei Kagaku Kaishi, Vol. 47, pp 201 and Published Examined Japanese Patent Application No. 3298/1975, but no description on the synthesis of the mono(2-propynyl)-substituted compound of the present invention is shown in the literature.

An attempt was made to synthesize mono(2-propynyl)-substituted ester using magnesium alkoxide as a base and 2-propynyl chloride which is cheaper and easier to handle, but the progress of the replacement reaction was extremely slow, and besides the selectivity of the reaction and the yield of the objective mono-(2-propynyl)-substituted ester were extremely low.

For the reasons as described above, the inventors extensively studied a method for producing mono(2-propynyl)-substituted acetonedicarboxylic esters of the formula (VI) with a good selectivity and in a high yield using an industrially advantageous 2-propynyl chloride. As a result, the following were found: In the reaction between 2-propynyl chloride and an acetonedicarboxylic ester of the formula (VII) using magnesium alkoxide as a base, use of alkali iodide as a catalyst promotes the smooth progress of the reaction, elevates the yield and selectivity of the monosubstituted product and besides improves the reaction to a large extent as compared with the use of 2-propynyl bromide. The inventors made a further study of this method and completed the present invention.

It is generally well known that various substituted products such as mono-, di-, tri- and tetra-substituted ones are produced in the replacement reaction of acetonedicarboxylic esters. Consequently, elevating the selectivity of the monosubstituted product is very important. Generally, when starting materials and by-products in the resulting product are not related to the subsequent reactions, the impurities in the crude product cause no serious problems.

As in the case of the reaction of the present invention, however, when there is a possibility that components having the same property are produced at the same time, the components show the same behavior in the subsequent reactions to cause the lowering of the purity and yield of the objective product. In order to avoid this disadvantage, the starting material for the next reaction should be of a high purity. In the case of a reaction system, however, wherein the selectivity of the reaction itself is low and the starting material and by-products are similar to the objective product in the chemical and physical properties, the separation of the objective product is very difficult. Even though there is a separation technique, the technique itself is very complicated and the yield of the objective product decreases to a large extent. If it is therefore possible to elevate the selectivity of the objective product to such a degree that a special purification technique will not be required, not only is the separation technique simplified, but a great improvement in economy is also effected. From the standpoint described above, it may be said that the method of the present invention has a very great significance.

In the conventional replacement reactions using reactive organic chlorides, it is well known that the reactivity of the chlorides is elevated by using sodium iodide as a catalyst. However, the main object of the use of this catalyst is to elevate the rate of reaction as is also shown, for example, in "Reagents for Organic Synthesis, pp. 1088". Consequently, the information obtained by the present invention that the use of this catalyst promotes the selective formation of the monosubstituted product and elevates the yield of the product, is a surprising fact.

In carrying out the present invention, the reaction time is within a range of preferably 1 hour to 50 hours, and the reaction temperature is within a range of generally from 0° C. to the boiling point of the solvent, preferably from room temperature (e.g. 20° C.) to the boiling point of the solvent. The alkali iodide used includes potassium iodide, sodium iodide and lithium iodide. Of these compounds, lithium iodide is particularly preferred. The amount of alkali iodide is within a range of preferably 5 to 20 mole % based on acetonedicarboxylic ester (VII). Of course, alkali iodide includes those which are produced in situ in the reaction system.

Generally, the solvent used is the same alkanol as that constituting magnesium alkoxide, but an inert organic solvent may be added. The amount of magnesium alkoxide is within a range of preferably 1 to 3 moles based on acetonedicarboxylic ester (VII).

As described above, the present invention provides a method for easily producing cyclopentenolone of the formula (I), δ-diketone of the formula (V) and the mono(2-propynyl)-substituted ester of the formula (VI) which are important intermediates for producing agricultural chemicals. The role of the present invention is extremely great at the present time at which easy and advantageous methods for producing the cyclopentenolone are not known at all.

Next, the present invention will be illustrated in more detail with reference to the following examples. But the present invention is not of course limited to these examples.

[Stage A]

Example 1

An aqueous sodium hydroxide solution (sodium hydroxide 1.6 g, water 30 ml) was cooled to −5° C., and a solution of 2,5-dioxo-3-hydroxy-8-nonyne of the formula (V) (3.0 g) in toluene (50 ml) was added dropwise thereto with stirring over 2 hours.

Thereafter, the reaction solution was stirred at −5° C. for further 2 hours and then adjusted to a pH of 7 with 10% aqueous hydrochloric acid. The aqueous portion of the reaction solution was saturated with sodium chloride, followed by separation into aqueous and organic layers. The aqueous layer was extracted two times with ethyl acetate, and the ethyl acetate layer and the foregoing toluene layer were combined. The solvent was then removed by evaporation, and the residual oil was distilled under reduced pressure to obtain 1.47 g of the objective 2-methyl-3-2'-propynyl-cyclopent-2-en-4-on-1-ol [the compound of the formula (I)] as a pale yellow oil (yield 55%).
Boiling point: 100°–110° C. (0.1 mmHg)
Refractive index: 1.5275 (23.5° C.)
NMR (solvent CDCl$_3$; internal standard TMS)
δ value: ppm
δ: 194 (t, 1H), 2.18 (s, 3H), 2.1–3.0 (m, 2H), 3.05 (d, 2H), 4.67 (dm, 1H)

[Stage B]

Example 2

To dimethyl 2-(2'-propynyl)-3-oxoglutarate (21.2 g) was added a 10% aqueous sodium hydroxide solution (sodium hydroxide 8.0 g, water 72 ml) with ice cooling, followed by stirring at 30° C. for 5 hours. The pH of the reaction solution was adjusted to 7.5 with a 10% sulfuric acid with ice cooling, and toluene (60 ml) was added thereto. While passing nitrogen stream, a 40.7% aqueous methylglyoxal solution (20 g) was added dropwise to the reaction solution at 35° C. over 2 hours. Thereafter, the reaction solution was stirred at 35° C. for 15 hours. The reaction solution was separated into two layers, and the aqueous layer was saturated with sodium chloride and extracted four times with ethyl acetate. The toluene layer and the ethyl acetate layer were combined, and the solvent was removed by evaporation to obtain 13.8 g of 2,5-dioxo-3-hydroxy-8-nonyne as a pale yellow oil (yield 82.0%).
$n_D^{17}$ 1.4581
NMR (CDCl$_3$, internal standard TMS, δ value): 1.94 (1H, t) 2.20 (3H, s), 2.1–3.0 (6H, m), 4.3 (1H, t).

EXAMPLE 3

To diethyl 2-(2'-propynyl)-3-oxoglutarate (24.0 g) was added a 10% aqueous sodium hydroxide solution (sodium hydroxide 8.0 g, water 72 ml) with ice cooling, followed by stirring at 30° C. for 5 hours. The pH of the reaction solution was adjusted to 7.5 with a 10% sulfuric acid with ice cooling, and toluene (60 ml) was added thereto. While passing nitrogen stream, a 40.7% aqueous methylglyoxal solution (20 g) was added dropwise to the reaction solution at 35° C. over 2 hours. Thereafter, the reaction solution was stirred at 35° C. for 15 hours. The reaction solution was separated into two layers, and the aqueous layer was saturated with sodium chloride and extracted three times with ethyl acetate. The toluene layer and the ethyl acetate layer were combined, and the solvent was removed by evaporation to obtain 14.1 g of 2,5-dioxo-3-hydroxy-8-nonyne as a pale yellow oil. Yield 83.8%. $n_D^{23}$ 1.4593.

Example 4

To an aqueous sodium hydoxide solution (sodium hydroxide 22.6 g, water 200 ml) was added dropwise dimethyl 2-(2'-propynyl)-3-oxoglutarate (50.0 g) with ice cooling, followed by stirring at 30° C. for 6 hours. The pH of the reaction solution was adjusted to 7.8 with a 10% sulfuric acid with ice cooling, and sodium hydrogen carbonate (1.2 g) and sodium hydrosulfite (3.2 g) were added. While passing nitrogen stream, a 42.5% aqueous methyl glyoxal solution (48.0 g) was added dropwise to the reaction solution at 35°–40° C. over 2 hours. Thereafter, the reaction solution was stirred at the same temperature for 6 hours. While passing nitrogen stream, this reaction solution was added dropwise to a mixed solution of toluene (100 ml) and an 10% aqueous sodium hydroxide solution (240 g) at 0° C. over 2 hours. Thereafter, the reaction solution was stirred at the same temperature, and then the reaction solution was neutralized with conc. hydrochloric acid. The reaction solution was saturated with sodium chloride and extracted two times with ethyl acetate. The ethyl acetate layer was concentrated and then distilled under reduced pressure to obtain 18.8 g of 2-methyl-3-(2'- propynyl)cyclopent-2-en-4-on-1-ol. (yield 60.0%) [Stage C]

Example 5

Magnesium (5.2 g; 1.5 times by mole based on methyl acetonedicarboxylate) was allowed to react with methanol (150 ml) in the presence of a catalytic amount of iodine. Methyl acetonedicarboxylate (2.5 g) was added thereto, and after stirring for 1.5 hours, lithium iodide (1.9 g; 0.1 time by mole based on methyl acetonedicarboxylate) and 2-propynyl chloride (11.24 g; 1.05 time by mole based on methyl acetonedicarboxylate) were added to carry out reaction at 60° C. for 4 hours. Thereafter, most of methanol was removed by evaporation, and ice, dilute hydrochloric acid, ethyl acetate and sodium chloride were added to extract the product. The extract was dried over magnesium sulfate and distilled to obtain 26.1 g of a fraction having a boiling point, 90°–101° C./0.2 mmHg. It was found by gas chromatography that the ratio of material to monosubstituted product to disubstituted product to others was 6.0:83.0:8.0:3.0. The yield of the monosubstituted product was 71.9%.

Examples 6 and 7

Substitution was carried out in the same manner as in Example 1 except that the kind of catalyst and reaction time were changed. The following results were obtained.

| Exp. No. | Catalyst | Reaction time (hour) | Material | Monosubstituted product | Disubstituted product | Others | Yield of monosubstituted product (%) |
|---|---|---|---|---|---|---|---|
| 6 | NaI (0.1 time by mole) | 10.5 | 9.0 | 81.0 | 7.0 | 3.0 | 62.7 |
| 7 | KI (0.1 time by mole) | 13 | 14.0 | 77.0 | 7.0 | 2.0 | 61.1 |

Reference Example 1

Dimethyl 3-oxoglutarate (25.0 g) was added to a methanol solution (150 ml) containing magnesium methoxide (prepared from 5.2 g of metallic magnesium). After refluxing with stirring for 1 hour, propargyl bromide (18.0 g) was added thereto, followed by stirring at 55° to 60° C. for 6 hours. After removing methanol by evaporation, ethyl acetate and dilute hydrochloric acid were added, followed by separation into two layers. The ethyl acetate layer was washed with aqueous sodium chloride and dried over magnesium sulfate. After removing ethyl acetate by evaporation, distillation under reduced pressure was carried out to obtain dimethyl 2-(2'-propynyl)-3-oxoglutarate.
Boiling point: 107°–108° C. (0.4 mmHg)
Refractive index: 1.4660 (24° C.)
Yield: 49%
NMR (CCl$_4$, internal standard TMS, $\delta$ value): 1.92 (t, 1H), 2.66 (dd, 2H), 3.61 (s, 2H), 3.81 (t, 1H), 3.66 (s, 3H), 3.70 (s, 3H).

Reference Example 2

Substitution was carried out in the same manner as in Example 5 except that the catalyst was not used, and that the reaction time was changed. The following result was obtained.

| Catalyst | Reaction time (hour) | Material | Monosubstituted product | Disubstituted product | Others | Yield of monosubstituted product (%) |
|---|---|---|---|---|---|---|
| None | 14 | 30.0 | 66.0 | <1.0 | 3.0 | 43.7 |

Reference Example 3

According to Example 5, magnesium ethoxide was prepared from magnesium of 1.5 times by mole based on ethyl acetonedicarboxylate, and then ethyl acetonedicarboxylate was allowed to react with 2-propynyl chloride of 1.05 time by mole based on ethyl acetonedicarboxylate at 78° C. for 8.5 hours in ethanol using the foregoing magnesium ethoxide. The subsequent treatment was the same as in Example 5. The following result was obtained.

| Catalyst | Reaction time (hour) | Material | Monosubstituted product | Disubstituted product | Others | Yield of monosubstituted product (%) |
|---|---|---|---|---|---|---|
| None | 8.5 | 6.5 | 70.0 | 16.0 | 7.5 | 53.5 |

What is claimed is:

1. A process for producing cyclopentenolone of the formula (I),

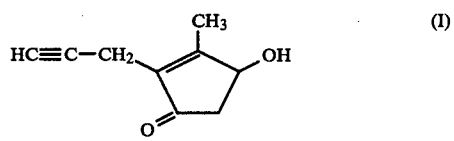

(I)

which comprises ring-closure reaction of $\gamma$-diketone of the formula (V),

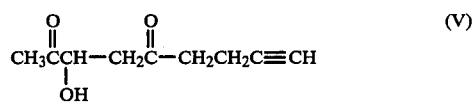

(V)

under alkaline conditions, at a temperature of $-30°$ C. to room temperature.

2. The process according to claim 1, wherein the alkaline condition is accomplished by a reagent for making the reaction system alkaline with an alkali, said alkali being a member selected from sodium hydroxide, potassium hydroxide, lithium hydroxide, sodium carbonate and potassium carbonate.

3. The process according to claim 1, wherein the reaction is carried out in a heterogeneous organic solvent/water system in the presence of a phase transfer catalyst.

4. The process according to claim 1, wherein the reaction solvent is water, methanol, ethanol, propanol, tetrahydrofuran, dioxane, dimethylformamide, dimethyl sulfoxide, benzene, toluene, xylene, hexane, chloroform or dichloromethane, or the mixture thereof.

5. The process according to claim 1, wherein the γ-diketone of the formula (V) is produced by hydrolyzing mono-(2-propynyl)-substituted acetonedicarboxylic ester of the formula (VI),

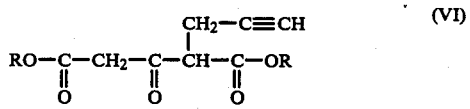 (VI)

wherein R is a $C_1$–$C_6$ alkyl group under an alkaline condition with an alkali and then reacting the hydrolyzed product with methylglyoxal of the formula

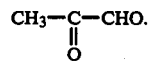

6. The process according to claim 5, wherein the alkaline condition is accomplished by addition of an alkali for making a reaction system alkaline, said alkali being a member selected from sodium hydroxide, barium hydroxide, lithium hydroxide and potassium hydroxide.

7. The process according to claim 5, wherein the reaction solvent is water, lower alcohol or hydrocarbon, or the mixture thereof.

8. The process according to claim 5, wherein the reaction is carried out at a temperature of −20° C. to the boiling point of the solvent.

9. The process according to claim 8, wherein the reaction is carried out at a temperature of 0° C. to 50° C.

10. The process according to claim 5, wherein the alkali is used in an amount of 2.0 to 4.0 moles based on 1 mole of the compound of the formula (VI).

11. The process according to claim 5, wherein methylglyoxal is used in an amount of 1.0 to 2.0 moles based on 1 mole of the compound of the formula (VI).

12. The process according to claim 5, wherein the reaction is carried out without the separation of the hydrolyzed product.

13. The process according to claim 5, wherein the reaction is carried out at pH of 7 to 8.

14. The process according to claim 5, wherein the mono-(2-propynyl)-substituted acetonedicarboxylic ester of the formula (VI) is produced by reacting an acetonedicarboxylic ester of the formula (VII),

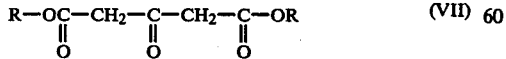 (VII)

wherein R is a $C_1$–$C_6$ alkyl group, with 2-propynyl chloride in the presence of magnesium alkoxide and in the presence of alkali iodide.

15. The process according to claim 14, wherein the reaction is carried out in the presence of alkali iodide.

16. The process according to claim 14, wherein the reaction solvent is the same alkanol as that constituting magnesium alkoxide.

17. The process according to claim 16, wherein the alkali iodide is potassium iodide, sodium iodide or lithium iodide.

18. The process according to claim 14, wherein the reaction is carried out at a temperature of 0° C. to the boiling point of the solvent.

19. The process according to claim 14, wherein the magnesium alkoxide is used in an amount of 1 to 3 moles based on 1 mole of the compound of the formula (VII).

20. The process according to claim 14, wherein the alkali iodide is used in an amount of 5 to 20 mole % based on 1 mole of the formula (VII).

21. A process for producing cyclopentenolone of the formula (I),

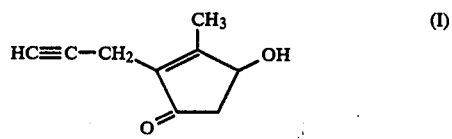 (I)

which comprises reacting an acetonedicarboxylic ester of the formula (VII),

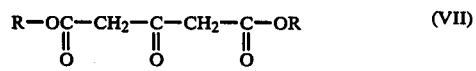 (VII)

wherein R is a $C_1$–$C_6$ alkyl group, with 2-propynyl chloride in the presence of magnesium alkoxide and in the presence of alkali iodide to obtain mono-(2-propynyl)-substituted acetonedicarboxylic ester of the formula (VI),

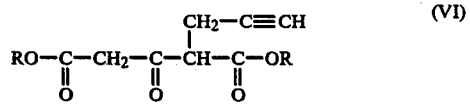 (VI)

wherein R is as defined above; hydrolyzing the mono-(2-propynyl)-substituted acetonedicarboxylic ester of the formula (VI) under an alkaline condition with an alkali and then reacting the hydrolyzed product with methylglyoxal of the formula,

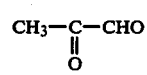

to obtain γ-diketone of the formula (V),

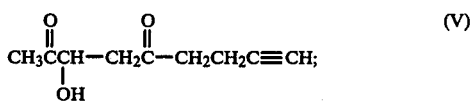 (V)

and ring-closing the γ-diketone of the formula (V) under alkaline condition.

* * * * *